United States Patent
Ott et al.

(10) Patent No.: US 6,556,851 B1
(45) Date of Patent: Apr. 29, 2003

(54) DETECTION PROBE FOR OPTICAL SPECTROSCOPY AND SPECTROMETRY

(75) Inventors: Lutz Ott, Fernwald (DE); Alfons Krug, Biebertal (DE)

(73) Assignee: LEA Medizintechnik GmbH, Giessen (DE)

( * ) Notice: Subject to any disclaimer, the term of this patent is extended or adjusted under 35 U.S.C. 154(b) by 0 days.

(21) Appl. No.: 09/856,181

(22) PCT Filed: Dec. 7, 1999

(86) PCT No.: PCT/EP99/09583
§ 371 (c)(1),
(2), (4) Date: Jun. 5, 2001

(87) PCT Pub. No.: WO00/33730
PCT Pub. Date: Jun. 15, 2000

(30) Foreign Application Priority Data

Dec. 7, 1998 (DE) .......................................... 198 56 246

(51) Int. Cl.[7] .................................................. A61B 5/00
(52) U.S. Cl. ........................ 600/310; 600/342; 385/117
(58) Field of Search ............................... 600/310, 342, 600/344; 385/117

(56) References Cited

U.S. PATENT DOCUMENTS

| | | | |
|---|---|---|---|
| 4,321,930 A | 3/1982 | Jobsis et al. | |
| 5,217,013 A | * 6/1993 | Lewis et al. | 128/633 |
| 5,259,382 A | 11/1993 | Kronberg | |
| 5,299,570 A | 4/1994 | Hatschek | |
| 5,584,296 A | * 12/1996 | Cui et al. | 128/633 |

FOREIGN PATENT DOCUMENTS

| | | |
|---|---|---|
| DE | 2517129 | 6/1976 |
| EP | 771546 | 5/1997 |

OTHER PUBLICATIONS

M. Cope & D. T. Delpy: "System for long–term measurement of cerebral blood and tissue oxygenation on newborn infants by near infra–red transillumination", Medical & Biological Engineering & Computing May 1988, pp. 289–294.

Weija Cui & Lee E. Ostrander: "In Vivo Reflectance of Blood and Tissue as a Function of light Wavelength", IEEE Transactions on Biomedical Engineering, Jun. 1990, No. 6, pp. 632–639.

* cited by examiner

Primary Examiner—Kevin Lee
(74) Attorney, Agent, or Firm—Charles P. Boukus, Jr.

(57) ABSTRACT

The invention relates to a detection probe for spectroscopy and/or spectrometry in tissue (4) with the aid of optical fibers (1,2). At least one fiber (2) transmits light into the tissue (4) and other fibers (2) receive backscattered light. According to the invention, deflection devices (mirrors 6, fibers 7, prisms 9,10,11) are provided for the light, whereby the inventive probe is substantially flatter and easier to handle.

12 Claims, 4 Drawing Sheets

DETECTION PROBE FOR OPTICAL SPECTROSCOPY AND SPECTROMETRY

BACKGROUND OF THE INVENTION

The invention relates detection probes for in depth resolving optical spectroscopy and spectrometry.

Various possibilities for detecting the light scattered in tissue in dependence on the distance from the source of illumination already exist. Apart from the use of photodetector arrays directly on the tissue surface, there is the possibility of transmitting the light to the detectors by an arrangement of light guides.

U.S. Pat. No. 4,321,930 discloses an apparatus for monitoring metabolisms in bodies, in which a probe which contains a plurality of deflecting devices, to be specific bent light guides, is placed on the skin.

A corresponding device is also known from DE-A-25 17 129, as a photoelectric pulse pick-up with fiber optics.

In a known configuration, as represented in FIG. 1 and described in EP 771 546 A2, optical fibers in a certain arrangement, which determines the depth of detection and the in-depth resolution, can be placed on the tissue in abutting manner. At the same time, the fibers (illumination fiber 1, detection fibers 2) are cemented into a corresponding fiber holder 3 (material: e.g. PEEK, high-grade steel) or fixed in relation to one another at previously defined spacings by a casting compound (e.g. epoxy casting compound Epo-Tek 301-2). For reasons of biocompatibility, corresponding materials must be used. Also shown in FIG. 1 is the tissue 4, into which light is coupled from the fiber 1, and the paths 5 of the scattered light, which is picked up by the individual detection fibers 2. Because of the relatively unfavorable leverage, such a detection probe must have a wide base plate to allow it to be fixed securely. The use of more than three fibers 1, 2 makes the feeding-in fiber optic cable quite rigid, resulting in great bending radii and consequently a great space requirement.

The direct coupling of the scattered light into the fiber makes the known arrangement very effective. However, this is at the expense of convenient handling and fixing. With this type of optical detection, a fiber diameter beginning from 50 μm is adequate in the case of a fiber spacing of 0.3 mm.

BRIEF SUMMARY OF THE INVENTION

Against this background, it is an object of the invention to reduce the overall size of the detection probe and improve handling.

A detection probe with the features of claim 1 is proposed to achieve this object. Configurations of the invention are the subject of subclaims.

An orthogonal detection of the scattered light is preferably provided, with a fiber guided parallel to the tissue surface and with a deflection of the light of between 0° and 180°, preferably by 90°, with at least one mirror surface.

The invention allows the detection probes to be made especially flat, thereby reducing the overall size and improving handling. Electrodes can be easily fixed, in a way similar to the electrodes in the case of an electrocardiogram, and are also not felt to be a hindrance, since the "leads" lie flat against the body and do not protrude perpendicularly from it.

Further aims, advantages, features and application possibilities of the present invention emerge from the following description of an exemplary embodiment on the basis of the drawing. All the features described and/or graphically presented here form the subject-matter of the present invention in themselves or in any desired meaningful combination, even independently of how they are combined in the claims or the way in which the latter relate back to one another.

DETAILED DESCRIPTION OF THE INVENTION

Figure 1:
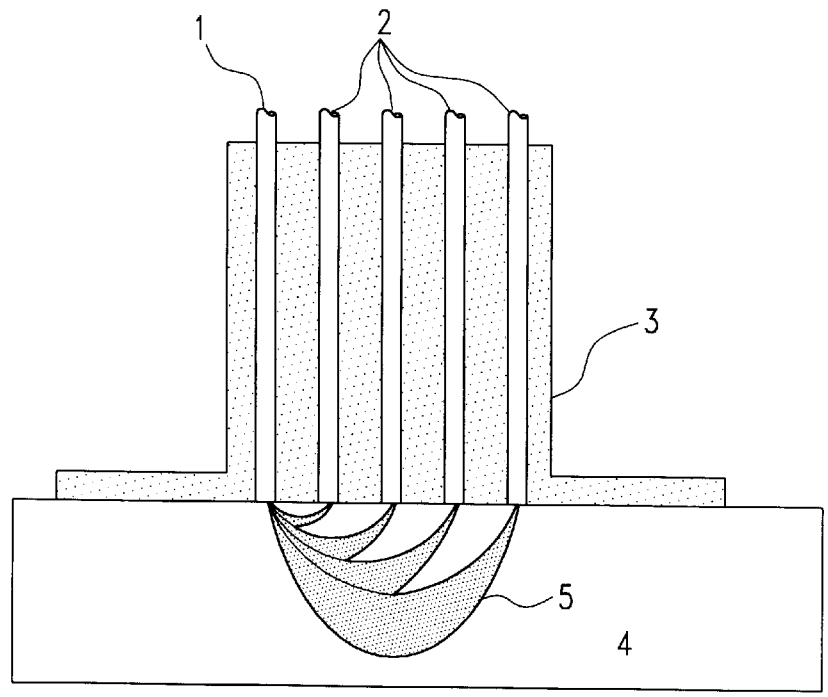
FIG. 1 is a cross-sectional view of a prior art probe.
Figure 2:
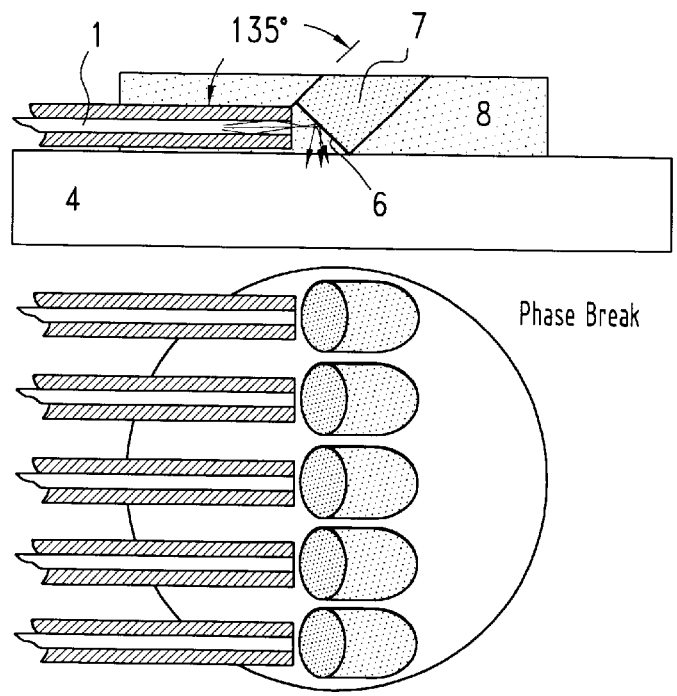
FIGS. 2, 3, 4, 5 and 6 respectively show embodiments of detection probes according to the invention.

In the case of the first exemplary embodiment according to FIG. 2, the deflection of the light is achieved by quartz fibers 7. For this purpose, the quartz fibers 1 and 2 for the illumination and the detection of the backscattered light, as in the case of the arrangement according to FIG. 1, are embedded in a casting compound 8, which forms a fiber holder 3.

According to the invention, the fibers 1 and 2 are not however guided perpendicularly with respect to the tissue surface, but run essentially parallel to the surface of the tissue 4. To deflect the light, quartz fibers 7 have been provided at the end of each fiber 1, 2, said quartz fibers being orthogonally ground at the end face, polished and subsequently mirrored. These faces form the surface mirrors 6, which deflect the light from the fiber 1 onto the tissue 4 and deflect the light backscattered from the depth of the tissue into the fibers 2. These quartz fibers 7 are cast together with the detection fibers 1, 2 at an angle of at least 100° to at most 170°, preferably 135°, with respect to the detection fibers 1, 2, so that the fiber ends of the fibers 7 form mirrors. This arrangement can be produced in one casting operation. However, the mounting of the fibers 7 is critical in respect of displacement, since the mirrored fibers 7 are only slightly larger than the detection fibers 1 and 2. In this way, probes with a height of approximately 3 mm can be produced. The required diameter depends on the fiber spacing and consequently on the desired depth detection. Because of the distance of the fiber ends from the tissue surface, the spatial resolution is slightly reduced, i.e. the detected surface area is increased in a way corresponding to the numerical aperture of the fiber and the distance between the tissue surface and the fiber end. During the reflection at the mirrored faces, some light is lost, which has an effect on both the illumination and the detection.

Figure 3:
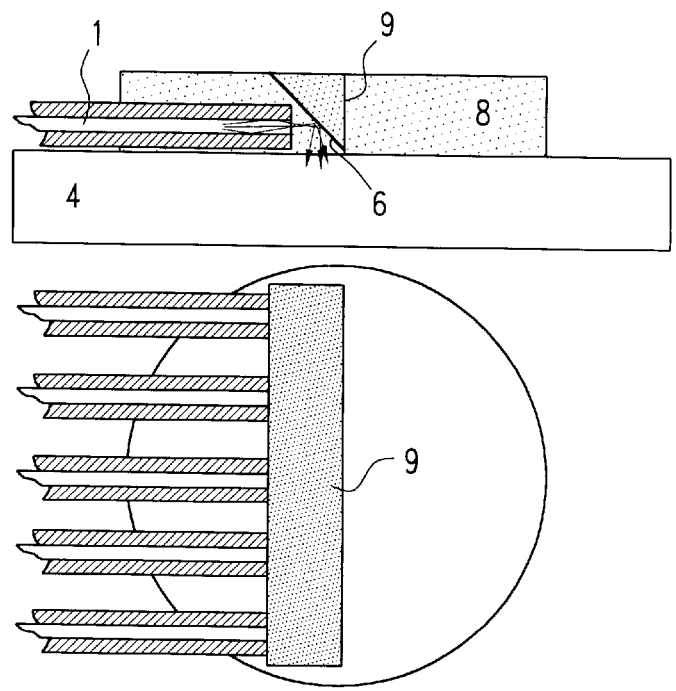

In the case of the second exemplary embodiment according to FIG. 3, the deflection of the light is achieved by a mirrored prism 9. A mirrored prism 9 is provided to avoid the adjustment of the fiber ends 7 according to the first exemplary embodiment, which is sensitive to displacement. The prism 9 is cast together with the fibers 1, 2 at a slight distance from them. The deflecting surface mirror 6 lies on the side of the glass prism 9 facing the fibers 1, 2 and the tissue 4. The light deflection takes place on the outer side of the prism 9. With knowledge of this and the above configuration, a different planar mirror (not shown) may also be used instead of the fiber ends 7 or the prism 9,-but must be correctly adjusted, which is easier when the prism 9 is used.

In this configuration too, only one casting operation is required for producing an epoxy casting compound 6 holding all the components. The mounting method with a prism is not sensitive in terms of adjustment, but the production of the prisms 9 with an edge length of approximately 2 mm and a length of 5–8 mm is very complex. Otherwise, this arrangement has the same properties as that according to the first exemplary embodiment according to FIG. 2.

Figure 4:
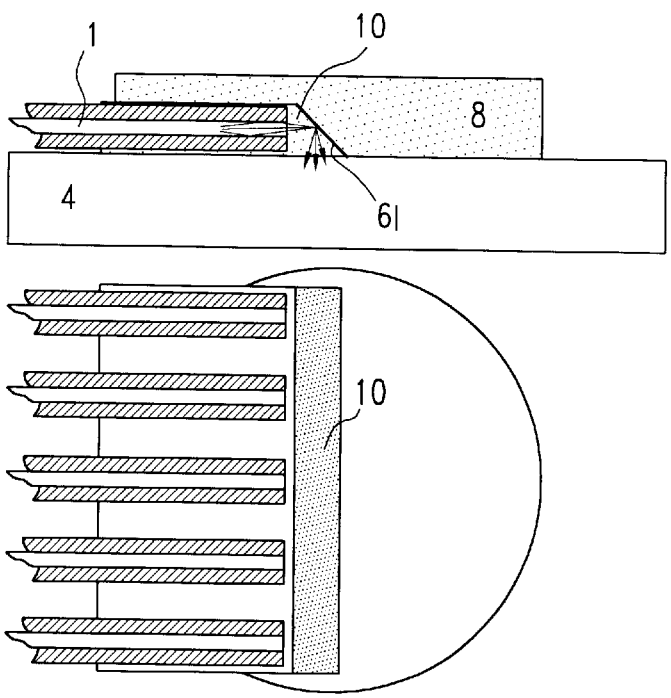

In the case of the third exemplary embodiment according to FIG. 4, the deflection of the light is achieved by an epoxy prism 10 cast onto the fiber ends of the fibers 1, 2. In this case, the fibers are cast at the desired spacing with protruding epoxy casting compound in a cuboidal form. The end of this epoxy block is ground with respect to the fiber axis at at least 100° to at most 170°, preferably at 135°, polished and reflectively coated, whereby the reflecting mirror is produced. The mirroring consequently takes place here within the prism 10. In a second casting operation, the supporting plate is cast. This is required for protecting the reflective coating. The grinding of the prism on the epoxy cuboid is very much easier than the grinding of a mini prism made of glass. If the casting mold is carefully made, it is even possible to dispense with the grinding and polishing of the mirror face.

Figure 5:
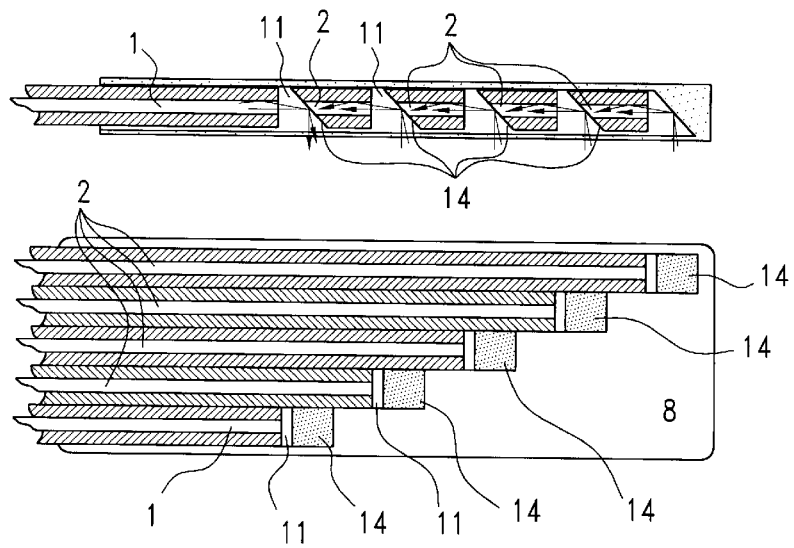

In the case of the fourth exemplary embodiment according to FIG. 5, the deflection of the light is achieved by a plurality of cast-on epoxy prisms 11 at offset fibers 1 and 2. Each of the prisms 11 in turn contains a reflecting coating.

For endoscopic use, the probe for the in-depth resolved detection of the laser Doppler signal must be miniaturized. A diameter of <3 mm must be aimed for, to be able to use the working channel of generally customary endoscopes. To ensure the in-depth resolution, the spacings of the detection fibers 2 cannot be reduced unlimitedly to any desired extent however.

In the case of the fiber arrangements of FIGS. 2 to 4, the diameter or the lateral extent of the detection probe is primarily determined by the distance between the fibers 2. For relevant detection depths of several millimeters, the diameter must not be less than 2 mm. This means that these designs are not suitable for endoscopic use. According to FIG. 5, the required detection distance can be achieved by axially offsetting the fibers 1, 2. For this purpose, a prism 11 must be cast onto each fiber 1, 2. With a suitable casting mold, this can take place in one operation for all the fibers 1, 2. The prisms 11 must be mirrored. To protect the reflective layer 14, the bundle of fibers must once again be cast into a thin jacket.

FIG. 5 shows a further possibility for deflecting light perpendicularly with respect to the fibers of the sensor, it being possible with this technology to achieve a wide range of angles.

The technology of FIG. 5 is based on the possibility of being able to design virtually any desired light guide structures on the basis of PMMA materials. This makes it possible for deflecting angles which previously could not be achieved due to restricted bending radii of the fibers to be produced by using structuring techniques.

Figure 6:
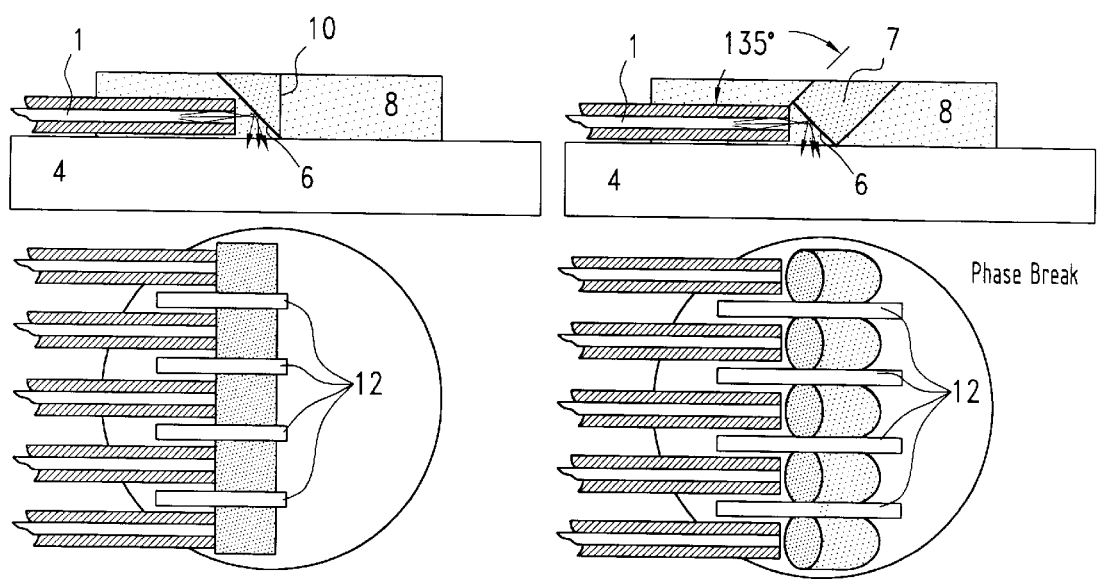

The exemplary embodiments according to FIGS. 2, 3, 4 are supplemented by a system of chambers according to FIG. 6, which prevents the undesired transfer of light from one measuring channel to the next already directly in the sensor head. A decisive factor is the interruption in the light distribution from one channel to the other channel between the obliquely directed reflecting faces 6 (in the left-hand part of the figure the faces 6 of the prisms 10, in the right-hand part of the figure the ends 6 of the quartz fibers 7) by means of a good absorber 12 or a reflector. It is important to avoid light passing from one channel to the other. This can take place by means of opaque materials or by slits which prevent light from being transmitted further. The rear side of the sensor preferably consists of a material with high broadband absorbency.

Figure 7:
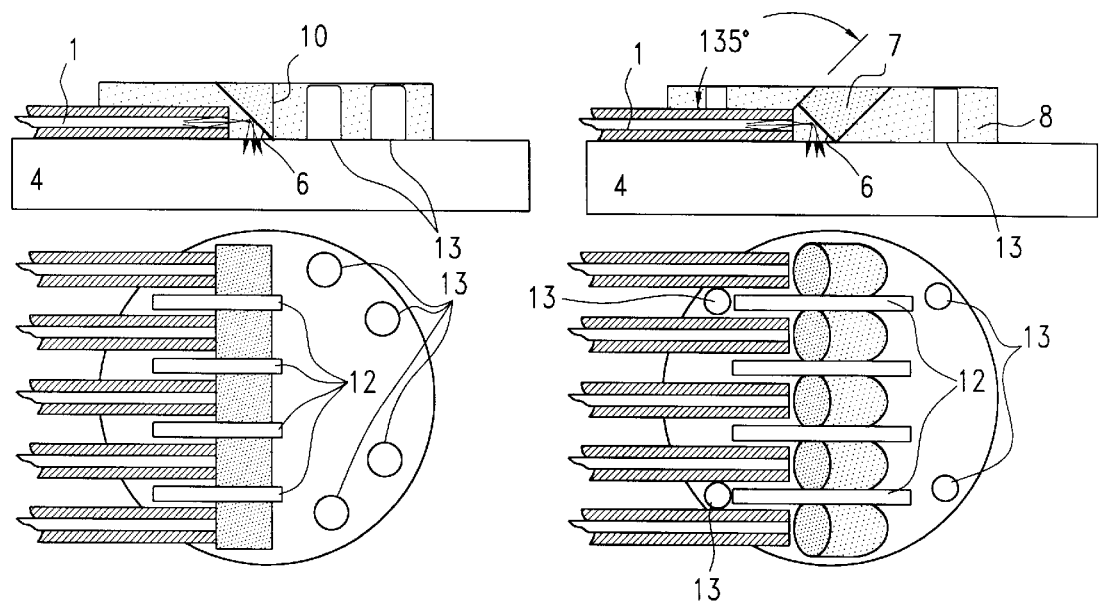
FIG. 7 shows probes with fixing possibilities.

In a way corresponding to FIG. 7, for applications in cardiology and internal medicine, holes or eyelets 13 may be provided at the edge of the probe in the casting compound 8, with or at which the sensor is sewn onto the myocardium or other internal organs for fixing. The arrangement of the holes or eyelets 13 is freely selectable.

For use in clinical practice, it is desirable to dispense with the use of the foot-operated switch for the deliberate switching on of the laser power, in order that protracted examinations can also be carried out. The safety concept developed for this purpose provides that only harmless LED light is emitted by means of two additional channels and is captured again by means of a detection fiber. The emitted LED light can only be detected if the sensor head is resting on the tissue. Consequently, this safety circuit has the effect that the laser source is only switched on if the sensor is resting on the tissue and not if it is emitting into free space, and in this case could unintentionally cause damage. In the case of the sensors required here, the corresponding number of channels must be integrated.

The additional advantage of this embodiment is that the requirements to be overcome for CE approval are lower, since it is possible to dispense with the foot-operated switch and the sensor head can now just contain optical signals and not electrical signals. In this respect, the equipment comes into a lower class of protection with respect to the stipulated leakage currents.

What is claimed is:

1. A detection probe for optical spectroscopy or spectrometry in tissue, with optical fibers (1,2), at least one fiber (1) introducing light into the tissue (4) and other fibers (2) receiving backscattered light, characterized in that a plurality of reflecting deflecting devices are provided for the light, the transfer of light from one reflecting deflecting device to the next being prevented by the arrangement of one or more optical separating devices (12).

2. The detection probe as claimed in claim 1, characterized in that each fiber (1,2) undergoes a beam deflection, the deflection taking place in the range from 45 degrees to 135 degrees, and the fibers (1,2) being guided parallel to a surface of the tissue.

3. The detection probe as claimed in claim 1, characterized in that, for laser Doppler measurements, each beam deflection of a channel is independent of the others, so that no optical crosstalk occurs between the channels as a result of the beam deflection.

4. The detection probe as claimed in claim 1, characterized in that two fibers of the probe are also used for the determination of the distance of the probe from the tissue, amplitude-modulated, phase-modulated or amplitude-and-phase-modulated light being used as a transmitting light source.

5. The detection probe as claimed in claim 1, characterized in that, for tissue-spectrometric measurements, each beam deflection of a channel is independent of the others, so that no optical crosstalk occurs between the channels as a result of the beam deflection.

6. The detection probe as claimed in claim 1, characterized in that the reflecting deflecting devices comprise fixed or movable prisms (9, 10, 11).

7. The detection probe as claimed in claim 1, characterized in that the reflecting deflecting devices comprise fixed or movable mirrors (6).

8. The detection probe as claimed in claim 1, characterized in that the reflecting deflecting devices comprise fixed or movable lenses.

9. The detection probe as claimed in claim 1, characterized in that the reflecting deflecting devices comprise ground surfaces.

10. The detection probe as claimed in claim 1, characterized in that the reflecting deflecting devices comprise treated light guiding structures.

11. The detection probe as claimed in claim 1, characterized in that the reflecting deflecting devices comprise dedicated fibers (7).

12. The detection probe as claimed in claim 1, characterized in that the reflecting deflecting devices comprise light guiding strictures formed in index materials.

* * * * *

UNITED STATES PATENT AND TRADEMARK OFFICE
CERTIFICATE OF CORRECTION

PATENT NO.     : 6,556,851 B1
DATED          : April 29, 2003
INVENTOR(S)    : Lutz Ott et al.

It is certified that error appears in the above-identified patent and that said Letters Patent is hereby corrected as shown below:

Column 6,
Line 6, change "strictures" to -- structures --.

Signed and Sealed this

Fourth Day of May, 2004

JON W. DUDAS
*Acting Director of the United States Patent and Trademark Office*